| United States Patent [19] | [11] Patent Number: 4,981,964 |
|---|---|
| Nelson et al. | [45] Date of Patent: Jan. 1, 1991 |

[54] OLIGOMERIC POLYESTERS AND POLYAMIDES CONTAINING DIPIPERIDYL TRIAZINE GROUPS

[75] Inventors: Richard V. Nelson, Wilmington, Del.; John F. Stephen, West Chester, Pa.

[73] Assignee: ICI Americas Inc., Wilmington, Del.

[21] Appl. No.: 284,520

[22] Filed: Dec. 15, 1988

[51] Int. Cl.$^5$ ............... C07D 413/12; C07D 403/04; C08K 5/34

[52] U.S. Cl. ................... 544/113; 544/195; 544/198; 544/209; 544/207; 524/83; 524/100

[58] Field of Search .............. 544/195, 198, 209, 113, 544/207

[56] References Cited

U.S. PATENT DOCUMENTS

| | | | |
|---|---|---|---|
| 4,086,204 | 4/1978 | Cassandrini et al. | 544/198 |
| 4,108,829 | 8/1978 | Cassandrini et al. | 544/198 |
| 4,321,374 | 3/1982 | Morimura et al. | 544/198 |
| 4,331,586 | 5/1982 | Hardy | 544/198 |
| 4,348,493 | 9/1982 | Loffelman | 544/198 |
| 4,386,177 | 5/1983 | Loffelman | 544/198 |
| 4,578,472 | 3/1986 | Yoshimura et al. | 544/198 |
| 4,670,488 | 6/1987 | Maegawa et al. | 544/198 |

FOREIGN PATENT DOCUMENTS

| | | | |
|---|---|---|---|
| 0107615 | 9/1983 | European Pat. Off. | 544/195 |
| 0227640 | 9/1983 | European Pat. Off. | 544/195 |
| 2136805 | 3/1984 | United Kingdom | 544/195 |

*Primary Examiner*—John M. Ford
*Assistant Examiner*—J. Richter
*Attorney, Agent, or Firm*—William E. Dickheiser; Richard A. Rowe

[57] ABSTRACT

Oligomeric polyesters and polyamides containing dipiperidyl triazine moieties are effective light stabilizers for synthetic polymers and particularly polyolefins.

10 Claims, No Drawings

OLIGOMERIC POLYESTERS AND POLYAMIDES CONTAINING DIPIPERIDYL TRIAZINE GROUPS

The invention is directed to polymeric compositions which are resistant to degradation and discoloration when exposed to actinic radiation. In particular, it is directed to resins such as polypropylene, polyethylene, etc. which are stabilized with an effective amount of an oligomeric triazine-based compound which contains the 2,2,6,6-tetraalkylpiperidine moiety. The invention is further directed to a novel group of substances which are useful as additives for synthetic polymers which act to retard photodegradation.

Many synthetic organic polymers deteriorate rapidly when exposed to sunlight. To circumvent this rapid degradation many additives have been developed to stabilize these resins against the harmful radiation. Among these additives are UV absorbers such as the hydroxybenzophenones, the hydroxyphenylbenzotriazoles, the organonickel complexes which serve to quench excited states, and most recently the hindered amine light stabilizers (HALS). The HALS possess the 2,2,6,6-tetraalkylpiperidine group that is most commonly substituted in the 4-position and act as radical scavengers, thus inhibiting the degradation process. Among the requirements for a compound to be an effective light stabilizer are the need for it to be compatible with the resin in which it is to be incorporated, sufficiently nonvolatile so as to remain in the resin during and after processing at elevated temperatures and be resistant to extraction by water.

Although the compounds of the prior art are, in general, effective light stabilizers for synthetic organic polymers, none of these compounds completely satisfy the stabilization requirements of polymers in their wide variety of forms and applications. This is particularly true for those polymeric materials that are used in thin articles, such as fibers and films. Because of these deficiencies there remains a need for new substances which meet all these requirements more fully.

The present invention is directed to the stabilization of synthetic polymers by the incorporation of an effective amount of a novel triazine oligomer which possesses the polyalkylpiperidine moiety. The triazine-based HALS of the invention are selected from those described by Formula (I)

wherein T is the divalent group:

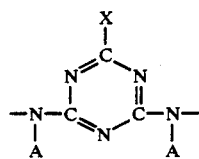

wherein A is:

-continued

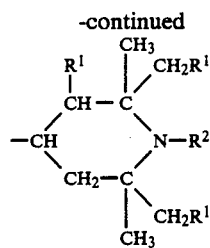

$R^1$ is selected from hydrogen and an alkyl group of 1–5 carbon atoms such as methyl, ethyl, n-propyl, etc., and is preferably hydrogen and methyl and most preferably hydrogen;

$R^2$ is selected from hydrogen, oxyl, hydroxyl, a straight or branched chain methylene-linked alkyl group of 1–18 carbon atoms such as methyl, ethyl, octyl, octadecyl, or 2-ethylhexyl, an alkanoyl group having 2–18 carbon atoms such as acetyl, propanoyl, butanoyl, isopentanoyl, or stearoyl, an alkenyl group of 3–4 carbon atoms, an alkenoyl group of 3–6 carbon atoms, an alkynyl group of 3–6 carbon atoms such as propargyl or 2-butynyl, a cyanomethyl group, an unsubstituted or substituted benzyl group of 7–15 carbon atoms, or a group as 3,5-di-tert-butyl-4-hydroxybenzyl, 3-tert-butyl-4-hydroxy-5-methylbenzyl, and a group —CH$_2$CH(OR$^3$)-R$^4$;

$R^3$ is selected from hydrogen, an aliphatic group of 1–18 carbon atoms, an araliphatic group such as benzyl and phenethyl, and an alkanoyl group having 2–18 carbon atoms;

$R^4$ is selected from hydrogen, an alkyl group of 1–16 carbon atoms and phenyl;

X is a group selected from hydrogen, halogen, hydroxyl, straight or branched chain alkyl having 1–18 carbon atoms, cycloalkyl having 5–12 carbon atoms, substituted or unsubstituted aryl having 6–18 carbon atoms, aralkyl having 7–18 carbon atoms, —N(R$^5$)(R$^6$), —OR$^7$, —SR$^7$ or —P(O)(OR$^8$)$_2$;

$R^5$ and $R^6$, same or different, can be selected from hydrogen, an alkyl group of 1–18 carbon atoms such a methyl, ethyl, isopropyl, butyl, octyl, dodecyl, and octadecyl, a cycloalkyl group of 5–12 carbon atoms such as cyclopentyl, cyclohexyl, cyclooctyl, and cyclododecyl, an aralkyl group of 7–11 carbon atoms such as benzyl and butylbenzyl, a 3–12 carbon alkyl group that may have in the chain a —O— or —N(R$^9$)-linkage, a hydroxyalkyl group having 2–4 carbon atoms, an acyloxyalkyl group having 3–15 carbon atoms, a group of the Formula A where R$^1$ and R$^2$ are as described above, or R$^5$ and R$^6$ together with the N-atom to which they are attached may form a heterocyclic ring such as pyrrolidino, piperidino or the ring formed may possess an —O— linkage to form a morpholino group;

$R^7$ is selected from an alkyl group of 1–18 carbon atoms, an alkenyl group of 3–12 carbon atoms, a cycloalkyl group of 5–12 carbon atoms, an aralkyl group of 7–11 carbon atoms, an alkyl group of 3–12 carbon atoms which possesses an —O— or in the chain, or an aryl group of 6–14 carbon atoms such as phenyl, naphthyl, 2,6-dimethylphenyl, etc.;

$R^8$ is selected from an alkyl group having 1–4 carbon atoms such as methyl, ethyl, propyl, etc.;

$R^9$ is selected from an alkyl group having 1–4 carbon atoms;

B is an alkylene group having 1–10 carbon atoms;

Y is selected from —O—, —N(H)—, and —N(R^10)— where $R^{10}$ represents an alkyl group of 1-20 carbon atoms or the group Formula A R is a divalent alkylene group of 2-20 carbon atoms which may be straight-chained or branched, wherein the alkylene group may be interrupted by —O—, —S— or —N(R^11)—, an alkyl group having 1-20 carbon atoms, a cycloalkylene group of 5-12 carbon atoms, a divalent group selected from

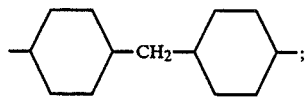

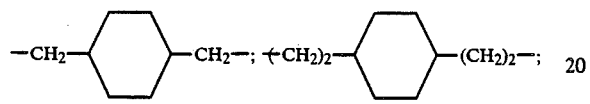

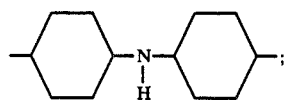

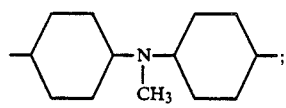

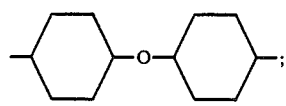

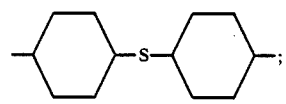

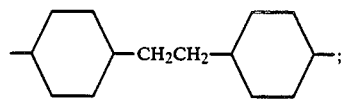

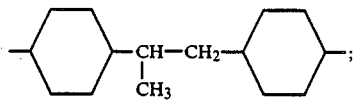

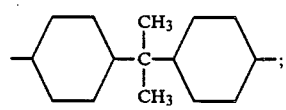

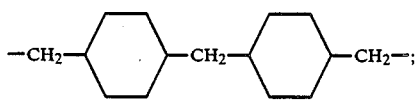

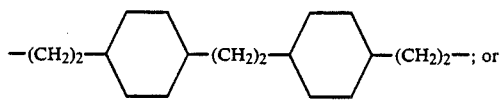

-continued

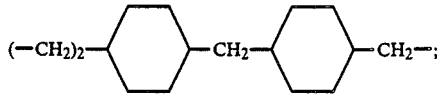

an arylene group of 6-12 group of carbon atoms, or an aralkylene group of 8-14 carbon atoms;

$R^{11}$ is an alkyl group of 1-18 carbon atoms, a cycloalkylene group of 5-12 carbon atoms or the group A;

$R^{12}$ is selected from a lower alkyl such as methyl, ethyl, propyl, and the like, or a group —R—Y—H where Y and R are as previously described;

$R^{13}$ is hydrogen; and m is an integer from about 1 to 40.

TABLE OF FORMULAS

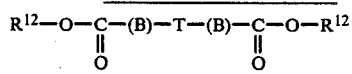 (II)

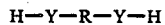 (III)

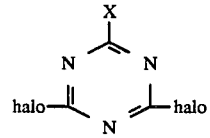 (IV)

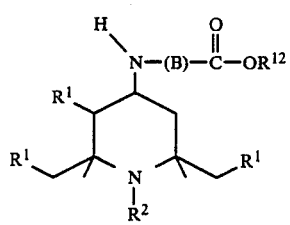 (V)

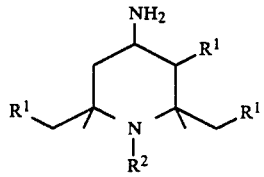 (VI)

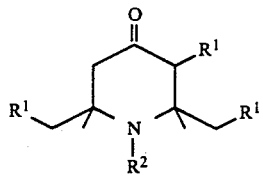 (VII)

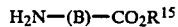 (VIII)

The oligomers of Formula (I) can be prepared by reaction of compounds of Formula (II) with those of Formula (III). The transesterification or amidation is generally run in the presence of an inert solvent such as xylene, toluene, and the like or neat depending upon the nature of the reactants. The reaction is generally carried out between 100° and 200° C. or when a solvent is used, at the reflux temperature of the solvent, in the presence of a basic catalyst such as lithium amide, titanium tetraisopropoxide, and the like, with removal of the generated alcohol. The products of Formula (I) are generally solids and can be isolated by solvent removal and subsequent purification where necessary.

Many of the compounds described by Formula (II) have been described in EP No. 107,615 (1984) and EP No. 226,640 (1987).

The compounds of Formula (II) can be prepared by the reaction of a compound of Formula (IV) with one of Formula (V). The reaction will generally be performed in the presence of an inert solvent such as dioxane, xylene, toluene, and the like at a reflux temperature of the solvent, especially between 100°-200° C., and in the presence of a scavenging base such as potassium carbonate, sodium hydroxide, sodium carbonate, and the like, for the removal of the generated hydrogen halide.

Illustrative examples of compounds of Formula (II) include but are not restricted to the following: 2-tert-butylamino-4,6-bis-((2,2,6,6-tetramethyl-4-piperidyl)ethoxycarbonylmethyleneamino)-1,3,5-triazine; 2-tert-octylamino-4,6-bis((2,2,6,6-tetramethyl-4-piperidyl)ethoxycarbonylmethyleneamino)-1,3,5-triazine, 2-morpholino-4,6-bis-((2,2,6,6-tetramethyl-4-piperidyl)ethoxycarbonylmethyleneamino)-1,3,5-triazine; 2-tert-octylamino-4,6-bis-(2,2,6,6-tetramethyl-4-piperidyl)-2-ethoxycarbonylethyleneamino)- 1,3,5-triazine; 2-(bis-2-hydroxyethyl)amino-4,6-bis((2,2,6,6-tetramethyl-4-piperidyl)ethoxycarbonymethyleneamino))-1,3,5-triazine; 2-tert-butylamino-4, 6-bis((2,2,6,6-tetramethyl-4-piperidyl)-2-methyl-2-ethoxycarbonylethyleneamino))-1,3,5-triazine; 2-methoxy-4,6-bis-((2,2,6,6,-tetramethyl-4-piperidyl)- ethoxycarbonylmethyleneamino)-1,3,5-triazine; 2-cyclohexyloxy-4,6-bis((2,2,6,6-tetramethyl-4-piperidyl)-ethoxycarbonylmethyleneamino)-1,3,5-triazine; 2-morpholino-4,6-bis-((1,2,2,6,6-pentamethyl-4-piperidyl)-methoxycarbonylmethyleneamino)-1,3,5-triazine; 2-tert-octylamino-4,6-bis-((2,2,6,6-tetramethyl-4-piperidyl)-methoxycarbonylmethyleneamino)-1,3,5-triazine; 2-tert-butylamino-4,6-bis-((2,2,6,6-tetramethyl-4-piperidyl-methoxycarbonylmethyleneamino)-1,3,5,-triazine, 2-dimethylamino-4,6-bis-((2,2,6,6-tetramethyl-4-piperidyl)-3-ethoxycarbonylpropylenemino)-1,3,5-triazine; 2-thiophenoxy-4,6-bis-((2,2,6,6-tetramethyl-4-piperidyl)methoxycarbonylmethyleneamino-1,3,5-triazine; 2-tert-octylamino-4,6-bis((1-acetyl-2,2,6,6-tetramethyl-4-piperidyl)ethoxycarbonylmethyleneamino)-1,3,5-triazine: 2-morpholino-4,6-bis-((1-hydroxy-2,2,6,6-tetramethyl-4-piperidyl)ethoxycarbonylmethyleneamino)-1,3,5-triazine; 2-tert-butyl-4,6-bis-((1-butyl-2,2,6,6-tetramethyl-4-piperidyl)methoxycarbonyl-methyleneamino)-1,3,5-triazine; 2-dimethylamino-4,6-bis((1-propargyl-2,2,6,6-tetramethyl-4-piperidyl)-2-ethoxycarbonylethyleneamino)-1,3,5-triazine; 2-methyl-4,6-bis-(2,2,6,6-tetramethyl-4-piperidyl)-ethoxycarbonylmethyleneamino- 1,3,5-triazine; 2-phenyl-4,6,-bis-((2,2,6,6-tetra-methyl-4-piperidyl)-3-methoxycarbonylpropyleneamino)-1,3,5-triazine and the like.

The preparation of 2-substituted-4,6-dihalo-1,3,5-triazines of the type described by those of the general Formula (IV) is well-known and are generally obtained by the regulated addition of the appropriate amine, alcohol or mercaptan to cyanuric chloride at a lowered temperature such as 0°14 5° C. in the presence of an inert solvent such as dioxane or acetone. In the case of the amine addition a scavenging base is used to react with the hydrogen halide which forms during the reaction. This scavenging base can be any of those mentioned above. The product is typically isolated by filtration and drying.

Illustrative examples of compounds of Formula (IV) include but are not restricted to the following: 2,4-dichloro-6-tert-butylamino-1,3,5-triazine; 2,4-dichloro-6-tert-octylamino-1,3,5-triazine; 2,4-dichloro-6-morpholino-1,3,5-triazine, 2,4-dichloro-6-methoxy-1,3,5-triazine; 2,4-dichloro-6-benzylamino-1,3,5-triazine: 2,4-dichloro-6-(2-hydroxyethylamino)-1,3,5-triazine; 2,4-dibromo-6-cyclohexylamino-1,3,5-triazine; 2,4-dibromo-6-diisopropylamino-1,3,5-triazine; 2,4-dichloro-6-(2-methoxyethoxy)-1,3,5-triazine; 2,4-dichloro-6-(bis-(2,2,6,6-tetramethyl-4-piperidinylamino))-1,3,5-triazine; 2,4-dibromo-6-tert-octylamino-1,3,5-triazine; 2,4-dichloro-6-pyrrolidinyl-1,3,5-triazine; 2,4-dichloro-6-ethoxycarbonylmethyleneamino-1,3,5-triazine; 2,4-dichloro-6-(2-propenyloxy)1,3,5-triazine; 2,4-dibromo-6-cyclohexyloxy-1,3,5-triazine; 2,4-dichloro-6-ethylthio-1,3,5-triazine; 2,4-dichloro-6-dodecylthio-1,3,5-triazine: 2,4-dichloro-6-(2-acetoxyethylamino)-1,3,5-triazine; 2,4-dichloro-6-dimethylphosphono-1,3,5-triazine; and the like.

The compounds of the Formula (V) can be obtained by the reaction of a compound of the Formula (VI) with the requisite haloacid (or salt) or haloester or via a Michael addition of Formula (VI) to the appropriate $\alpha,\beta$-unsaturated ester. Other methods which may be used to prepare these compounds include the reductive amination of compound VI with the requisite aldehyde such as $HCO(B) CO_2R^{14}$, where $R^{14}$ is hydrogen or lower alkyl or the reversed reductive amination involving a compound of Formula (VII) with the requisite amino acid or amino acid ester of Formula (VIII).

Some of the compounds of Formula (V) have been described in the prior art such as in the patents GB No. 2,136,805 (1983), DE No. 3,512,634 (1986), U.S. Pat. Nos. 4,578,472, and 4,670,488.

The 4-aminopolyalkylpiperidines of Formula (VI) used as intermediates for conversion to compounds of the invention are known from U.S. Pat. No. 3,684,765 and in general are prepared by the reduction amination of the corresponding ketone using either ammonia or the amine of interest.

The 4-oxopiperidines of Formula (VII) can be prepared by the reaction of ammonia with an aliphatic ketone. The reaction of ammonia with acetone to yield triacetoneamine is well known and various processes exist in the art for its manufacture. The reaction of ammonia with methyl ethyl ketone has been described by W. Traube in Chem. Ber. 41,777 (1908).

Compounds of the Formula (VII) that have other alkyl substituents in the 2-position and the 6-position can be prepared in a two-step process following the procedures outlined in Helv. Chim. Acta 30,1114 (1947) and Monatsh. Chem. 88, 464 (1957), followed by hydrolysis of the resulting pyrimidine.

In the examples of the invention where $R^2$ is other than hydrogen the additional derivatization can be carried out on the compounds of Formula (II). An alternative manner to perform the substitution is to derivatize as desired the compound of Formula (VII) and then introduce the 4-amino substituent by reductive amination.

The reductive amination can be carried out in the manner that has been well described in the prior art and primary literature. In general any catalyst that is commonly used in catalytic hydrogenation reactions can be used. Preferred catalysts include palladium on carbon and platinum on carbon. The reaction is normally run in the presence of a solvent. Suitable solvents include methanol and ethanol as well as others. The hydrogenation is usually carried out at a hydrogen pressure of 1-10 atmospheres and at a temperature necessary to achieve the reduction. In general the reduction can be achieved at ambient temperature but in some instances up to about 100° C. may be used.

The introduction of an alkyl, alkenyl, alkynyl and aralkyl at $R^2$ can be achieved by reaction of the initially prepared ketone of Formula (VII) or the derivatized triazine of Formula (II) which contain the free N-H of the piperidine with the suitable halide. Examples of suitable halides include methyl iodide, methyl chloride, ethyl bromide, dodecyl chloride, octadecyl chloride, allyl bromide, methyallyl chloride, butenyl chloride, propargyl chloride, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

The introduction of an alkanoyl or an alkenoyl group at $R^2$ can be performed by acylation of the N—H group using the suitable acid halide or, when convenient, the acid anhydride. If the acid halide is used the generated hydrogen halide can be scavenged in the same manner as stated previously. Examples of such groups are acetyl chloride, acetic anhydride, propionic anhydride, hexanoyl chloride, dodecanoyl chloride, and octadecanoyl chloride.

For $R^2$ as the group —$CH_2CH$—($O$—$R^3$)—$R^4$ the substituent can be introduced by reaction of the parent N-H compound with the corresponding alkylene oxide such as ethylene oxide, propylene oxide and styrene oxide. The resulting hydroxy compound can be acylated in the manner commonly known in the art using the suitable acid halide and can be alkylated by formation of the alkoxide and reaction with the desired alkyl halide.

For $R^2$ as the oxyl group or hydroxyl group the parent N—H compound can be treated with an oxidizing agent such as hydrogen peroxide in the presence of a catalyst like sodium tungstate or with a percarboxylic acid like metachloroperbenzoic acid, with subsequent reduction of the oxyl by catalytic hydrogenation if the hydroxyl is desired.

The following 15 compounds which serve to illustrate but not limit this invention are effective light stabilizers for synthetic organic polymers. The following examples are offered to demonstrate but not limit the scope of the invention:

1. 2-tert-octylamino-4,6-bis(2,2,6,6-tetramethyl-4-piperidyl)ethoxycarbonylmethyleneamino-1,3,5-triazine, oligomeric ester with 2,2-dimethyl-1,3-propanediol,
2. 2-tert-butylamino-4,6-bis-(2,2,6,6-tetramethyl-4-piperidyl)ethoxycarbonylmethyleneamino-1,3,5-triazine, oligomeric ester with 2,2-dimethyl-1,3-propanediol,
3. 2-morpholino-4,6-bis-(2,2,6,6-tetramethyl-4-piperidyl)ethoxycarbonylmethyleneamino-1,3,5-triazine, oligomeric ester with 2,2-dimethyl-1,3-propanediol,
4. 2-diallylamino-4,6-bis-(2,2,6,6-tetramethyl-4-piperidyl)ethoxycarbonylmethyleneamino-1,3,5triazine, oligomeric ester with 2,2-dimethyl-1,3-propanediol,
5. 2-tert-octylamino-4,6-bis((2,2,6,6-tetramethyl-4-piperidyl)-2-ethoxycarbonylethyleneamino)-1,3,5-triazine, oligomeric ester with 2,2-dimethyl-1,3-propanediol,
6. 2-tert-octylamino-4,6-bis-(2,2,6,6-tetramethyl-4-piperidyl)ethoxycarbonylmethyleneamino-1,3,5triazine, oligomeric ester with 1,6-hexanediol,
7. 2-morpholino-4,6-bis-(2,2,6,6-tetramethyl-4-triazine, oligomeric ester with 1,6-hexanediol,
8. 2-tert-butylamino-4,6-bis(2,2,6,6-tetramethyl-4-triazine, oligomeric ester with ethylene glycol,
9. 2-morpholino-4,6-bis-(2,2,6,6-tetramethyl-4-piperidyl)ethoxycarbonylmethyleneamino-1,3,5-triazine, oligomeric amide with 1,2-ethanediamine,
10. 2-tert-octylamino-4,6-bis-(2,2,6,6-tetramethyl-4-piperidyl)ethoxycarbonylmethyleneamino-1,3,5triazine, oligomeric amide with 1,6-hexanediamine,
11. 2-morpholino-4,6-bis-(1,2,2,6,6-pentamethyl-4-piperidyl)ethoxycarbonylmethyleneamino-1,3,5-triazine, oligomeric ester with 1,4-butanediol,
12. 2-tert-butylamino-4,6-bis((2,2,6,6-tetramethyl-4-piperidyl)-2-methyl-2-ethoxycarbonylethyleneamino)-1,3,5-triazine, oligomeric ester with 1,6 hexanediol,
13. 2-methoxy-4,6-bis-(1-acetyl-2,2,6,6-tetramethyl-4-piperidyl)ethoxycarbonylmethyleneamino-1,3,5-triazine, oligomeric ester with 2,2-dimethyl-1,3-propanediol,
14. 2-dimethylphosphono-4,6-bis-(2,2,6,6-tetramethyl-4-piperidyl)ethoxycarbonylmethyleneamino-1,3,5-triazine, oligomeric ester with 2,2-dimethyl-1,3-propanediol,
15. 2-ethoxy-4,6-bis-((2,2,6,6-tetramethyl-4-piperidyl)-3-ethoxycarbonylpropyleneamino)-1,3,5-triazine, oligomeric ester with 1,4-cyclohexanedimethanol, The compounds of this invention are effective light stabilizers for synthetic organic polymers. In addition to their effective light stabilizing properties some of the compounds of this invention also exhibit excellent thermal stabilizing performance. Among the synthetic organic polymers which can be stabilized by the compounds of this invention are the polyolefins which include homopolymers of olefins like polyethylene, both high- and low-density polyethylene, polypropylene, polybutadiene, polystyrene, and the like; and copolymers of olefins with other ethylenically unsaturated monomers such as ethylenepropylene copolymer, ethylene-butylene copolymer, ethylene-vinyl acetate copolymer, styrene butadiene copolymer and the like; terpolymers such as acrylonitrile-butadiene-styrene and the like; polyvinyl chlorides, polyvinylidene chlorides, copolymers of vinyl chloride and vinylidene chloride with vinyl acetate or other ethylenically unsaturated monomers; polyacetals such as polyoxymethylene and polyoxyethylene, polyesters such as polyethylene terephthalate; polyamides such as polyamide 6, polyamide 6,6, polyamide 6,10; polyurethanes and polymers derived from unsaturated acids and derivatives thereof; polycarbonates: polyacrylates and polymethacrylates, polyacrylic amides and polyacrylonitrile, as well as copolymers of acrylic acid and one or more of its derivatives with a melamine-formaldehyde resin.

Of particular importance among these groups of polymers is the stabilization of polyolofins. The compounds of this invention are excellent for their stabilization in an amount ranging from 0.01 to 5.0% by weight based on the weight of the polymer to be stabilized. Preferably they may be used in an amount between 0.05 and 1% by weight.

The compounds of the invention may also be used in conjunction with other stabilizers for the preparation of stabilized resin compositions. Among these other additives may be antioxidants, supplemental light stabilizers such as UV absorbers or other hindered amines, metal deactivators, etc., pigments, colorants, fillers, flame retardants, anti-static agents, and the like.

Suitable antioxidants include, those of the hindered phenol type such as 2,6-di-t-butyl-p-cresol; 4,4'-bis(2,6-diisopropylphenol); 2,4,6-tri-t-butylphenol: 2,2'-thiobis(4-methyl-6-t-butylphenol); octadecyl-3-(3',5'-di-t-butyl-4'-hydroxyphenyl) propionate; pentaerythrityl tetrakis(3-(3,5-di-t-butyl-4-hydroxyphenyl) propionate); 1,3,5-tris(3',5'-di-t-butyl-4'-hydroxybenzyl)isocyanurate; 1,3,5-tris-(2,6-dimethyl-4-t-butyl-3-hydroxybenzyl), isocyanurate; 3,5-di-t-butyl-4-hydroxyhydrocinnamic acid triester with 1,3,5-tris-(2-hydroxyethyl)-s-triazine-2,4,6-(1H,3H,5H)-trione; Esters of thiodipropionic acid such as dilaurylthiodipropionate and distearylthiodipropionate, etc.; Phosphites such as triphenyl phosphite, trinonylphenyl phosphite, distearyl, pentaerythritol diphosphite, diphenyldecyl phosphite, tris-(2,4-di-t-butylphenyl) phosphite, bis(2,4-di-t-butylphenyl)pentaerythritol diphosphite, etc.; supplemental light stabilizers such as those of the benzotriazole class including 2-(2'-hydroxy-3',5'-t-octylphenyl)benzotriazole; 2-(2'-hydroxy-3',5'-di-t-butylphenyl)-5-chlorobenzotriazole; 2-(2'-hydroxy-5'-di-t-methyl-phenyl)benzotriazole; 2-(2'-hydroxy-3'-t-butyl-5'-methylphenyl)benzotriazole; 2-(2'-hydroxy-3',5'-di-t-amylphenyl)benzotriazole; those of the hydroxybenzophenone type such as 2-hydroxy-4-methoxybenzophenone; 2-hydroxy-4-octyloxybenzophenone; 2,2'-dihydroxy-4-4'-dimethoxybenzophenone: Esters of hindered phenols such as n-hexadecyl-3,5-di-t-butyl-4-hydroxybenzoate and 2',4'-di-t-butylphenyl 3,5-di-t-butyl-4-hydroxybenzoate;

Metal complexes such as nickel complexes of 2,2'-thiobis-(4-tert-octylphenol), nickel dibutyl thiocarbamate; nickel salts of 3,5-di-t-butyl-4hydroxy benzylphosphonic acid monalkyl esters where alkyl is methyl, ethyl, etc., and methylphenylundecylketoneoxime.

Other examples of suitable supplemental light stabilizers may be found in U.S. Pat. Nos. 3,488,290 and 3,496,134.

The following examples are given to illustrate the present invention and are not meant to limit the nature or scope of the invention in any manner. FAB-MS analysis of the samples typically yielded value of m in the range of 1 to 8.

EXAMPLE 1

Preparation of Diethyl
2,4-bis-N-(2,2,6,6-tetramethyl-4-piperidyl)amino acetate-6-tert-octylamino-1,3,5-triazine, oligomer ester with 2,2-dimethyl-1,3-propanediol .

A mixture of diethyl 2,4-bis-N-(2,2,6,6-tetramethyl-4-piperidyl)aminoacetate-6-tert-octyl- amino-1,3,5-triazine (24.6 g, 35.6 mmol) and 2,2-dimethyl-1,3-propanediol (3.8 g, 35.6 mmol) was heated to about 135° C. under a gentle stream of nitrogen and the lithium amide catalyst (about 84 mg) was then added. The temperature of the reaction mixture was then increased to about 150°-160° C. and the heating was permitted to continue for about 8 hrs. After this time another 82 mg lithium amide was added and the reaction was continued for 4 hrs longer at 150°-160° C. Upon termination of the reaction the mixture was dissolved in CH$_2$Cl$_2$ and washed with water, brine and once again with water. The organic solution was dried (Na$_2$SO$_4$) and concentrated to yield an off-white solid weighing 24.9 and having a melting point of 165°-170° C. This material had a NMR spectrum consistent with that expected. VPO measurement gave a M$_n$ of about 1900.

EXAMPLE 2

Preparation of Diethyl
2,4-bis-N-(2,2,6,6-tetramethyl-4-piperidyl)aminoacetate-6-morpholino-1,3,5-triazine, oligomer with 2.2-dimethyl-1,3-propanediol This material was prepared in a manner essentially identical to that used for Example 1 with the exception that the reaction time was shortened to about 5 hrs and the temperature of the reaction was increased to about 170° C. Upon workup the material isolated (90% recovery) was a beige foam (m.p. about 89°-93° C.). This material yielded an NMR spectrum consistent with an, oligomeric mixture.

EXAMPLE 3

Preparation of Diethyl
2,4-bis-N-(2,2,6,6-tetramethyl-4-piperidyl)aminoacetate-6-tert-butylamino-1,3,5-triazine, oligomer with 2,2-dimethyl-1,3-propanediol This material was prepared in a manner essentially identical to that used for Example 1 with the exception that xylene was used initially to help minimize the loss of the diol due to sublimation. The catalyst was added while the mixture was at reflux and the solvent was then removed. The temperature of the mixture was increased to about 170° C. and the reaction was continued for about 8 hrs. During the reaction an additional portion of diol wa- added to replace some that was lost during the heating period. Upon workup the product was obtained as a beige foam (85% recovery) that sintered 108°14 120° C. The product had an NMR spectrum consistent with that expected for an oligomeric mixture.

EXAMPLE 4

Preparation of Diethyl
2,4-bis-N-(2,2,6,6-tetramethyl-4-piperidyl)aminoacetate-6-tert-octylamino-1,3,5-triazine, oligomer with 1,6-hexanediol This material was prepared in a manner very similar to that of Example 1 using 2.41 g (3.5 mmol) of the diethyl ester precursor and 0.41 g (3.5 mmol) of the hexanediol. The lithium amide catalyst (about 20 mg) was added when the mixture reached about 100° C. Heating was then continued to about 160°-170° C. and maintained for about 4 hrs. Upon workup the product was obtained as a beige foam (2.2 g, 85% recovery) with a m.p. of 108°-118° C. (sinters). The product has an NMR spectrum consistent with that expected for this oligomer mixture.

EXAMPLE 5

Preparation of Diethyl
2,4-bis-N-(2,2,6,6-tetramethyl-4-piperidyl)-aminoacetate-6-morpholino-1,3,5-triazine, oligomer with 1,6-hexanediol This material was prepared in a manner similar to that of Example 1 using 2.40 g (3.7 mmol) of the diethyl ester precursor and 0.44 g (3.7 mmol) of the hexanediol. The lithium amide catalyst (20 mg) was added when the temperature of the reaction mixture reached about 90°14 100° C. and the temperature was then increased to about 150° C. After stirring for 5 hrs and the addition of another small portion of the catalyst, the reaction was subjected to workup in the usual manner. The product was isolated as a just off-white foam (2.3 g, 90% recovery) having a m.p. of 53°-56° C. This product had an NMR spectrum consistent with that expected for the desired oligomer mixture.

EXAMPLE 6

Preparation of Diethyl 2,4-bis-N-(2,2,6,6-tetramethyl-4-piperidyl)aminoacetate-6-(2,2-bis hydroxy-ethylamino)-1,3,5-triazine, oligomeric ester with 2,2,-dimethyl-1,3,-propanediol This material was prepared in a manner similar to that of Example 1 using 1.96g (3.3 mmol) of the diethyl ester precursor and 0.37g (3.3 mmol) of 2,2-dimethyl-1,3-propanediol. The lithium amide catalyst (10 mg) was added when the temperature of the reaction mixture reached 120° C. The temperature was then increased to 170° C. and maintained for 16 hours. The mixture was cooled, partitioned between methylene chloride and water. The organic solution was dried ($Na_2SO_4$) and concentrated to yield 1.25 g of an off-white solid having a melting point of 86-95° C. The product had NMR spectrum consistent with that expected for this oligomeric mixture.

EXAMPLES 7-13

In order to further illustrate the effectiveness of the above-described compound as light stabilizers the oligomers made in Examples 1-6 were each incorporated into a commercially available polypropylene resin manufactured by Hercules Corporation as Pro-Fax 6301 Polypropylene Resin. The light stabilizers were incorporated into the polypropylene by solvent blending methylene chloride at a concentration of 0.25% by weight of the total resin composition. A primary antioxidant (stearyl β-(3,5-di-t-butyl-4-hydroxyphenyl)propionate) was used at a level of 0.2%. The resin was then extruded at 200° C. and compression molded at 6,000 psi at 188° C. to produce films having a thickness of 5 mils. A control film was also produced by an identical procedure with the light stabilizer omitted. Each film was exposed to a Xenon Arc in an Atlas Weather-o-Meter until the IR carbonyl increased by 0.5, which is considered to be the failure point.

TABLE 1

| Example # | Stabilizer | Hrs. to Failure |
|---|---|---|
| 7 | Control | 600 |
| 8 | Compound 1 | 4795 |
| 9 | Compound 2 | 4750 |
| 10 | Compound 3 | 3385 |
| 11 | Compound 4 | 4950 |
| 12 | Compound 5 | 3650 |
| 13 | Compound 6 | 4100 |

EXAMPLES 14-20

In order to illustrate the effectiveness of the above compounds for thermal stabilization the plaques prepared in the same manner as above were placed in a forced draft oven at 150° C. Failure was determined when the first signs of decomposition were charged as evidenced by flaking and/or crumpling of the plaque. Tests were run in quadruplicate and an average value was determined.

TABLE 2

| Example # | Stabilizer | Hrs. to Failure |
|---|---|---|
| 14 | Control | 108 |
| 15 | Compound 1 | 411 |
| 16 | Compound 2 | 312 |
| 17 | Compound 3 | 288 |
| 18 | Compound 4 | 288 |
| 19 | Compound 5 | 264 |
| 20 | Compound 6 | 342 |

What is claimed is:

1. A compound of the formula:

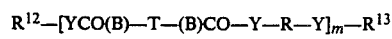

wherein T is the divalent group:

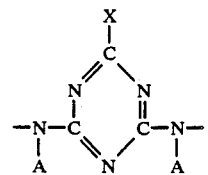

wherein A is:

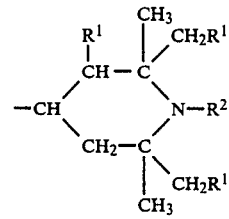

$R^1$ is selected from the group consisting of hydrogen and an alkyl group of 1-5 carbon atoms;

$R^2$ is selected from the group consisting of hydrogen, oxyl, hydroxyl, a straight or branched chain methylene, linked alkyl group of 1-8 carbon atoms, an alkanoyl group having 2-18 carbon atoms, an alkenyl group of 3-4 carbon atoms, an alkenoyl group of 3-6 carbon atoms, an alkynyl group of 3-6 carbon atoms, a cyanomethyl group, a benzyl group of 7-15 carbon atoms, and a group —$CH_2CH(OR^3)$—$R^4$; wherein:

$R^3$ is selected from the group consisting of hydrogen, a straight of branched chain methylene-linked alkyl group of 1-18 carbon atoms, an araliphatic group, and an alkanoyl group having 2-18 carbon atoms;

$R^4$ is selected from the group consisting of hydrogen, an alkyl group of 1-16 carbon atoms and phenyl;

X is hydrogen, halogen, hydroxyl, straight or branched chain alkyl group having 1-18 carbon atoms, cycloalkyl group having 5-12 carbon atoms, substituted or unsubstituted aryl group having 6-18 carbon atoms, aralkyl group having 7-18 carbon atoms, —$N(R^5)(R^6)$, —$OR^7$, —$SR^7$ or —$PO(OR^8)_2$ wherein:

$R^5$ and $R^6$, same or different, are selected from the group consisting of hydrogen, an alkyl group of 1-18 carbon atoms, a cycloalkyl group of 5-12 carbon atoms, an aralkyl group 7-11 carbon atoms, a 3-12 carbon alkyl group that may have in the chain an —O— or —$N(R^9)$-linkage, a hydroxyalkyl group having 2-4 carbon atoms, an acyloxyalkyl group having 3-15 carbon atoms, and a group of the Formula A where $R^1$ and $R^2$ are as described, or $R^5$ and $R^6$, together with N-atom to which they are attached, may form a heterocyclic ring optionally possessing an —O— linkage to form a morpholino group;

$R^7$ is selected from the group consisting of an alkyl group of 1–18 carbon atoms, an alkenyl group of 3–12 carbon atoms, a cycloalkyl group of 5–12 carbon atoms, an aralkyl group of 7–11 carbon atoms, or an alkyl group of 3–12 carbon atoms which possesses an —O— or —N($R^9$) in the chain, or an aryl group of 6–14 carbon atoms;

$R^8$ is selected from an alkyl group having 1–4 carbon atoms;

$R^9$ is selected from an alkyl group having 1–4 carbon atoms;

B is an alkylene group that is either straight chain or branched having 1–10 carbon atoms;

Y is selected from —O—, —N(H)—, and —N($R^{10}$)— where $R^{10}$ is an alkyl group of 1–20 carbon atoms or the group Formula A;

R is a divalent group of 2–20 carbon atoms, an alkylene group interrupted by —O—, —S— or —N($R^{11}$)—, a divalent group selected from

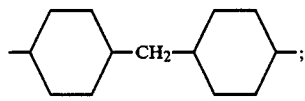

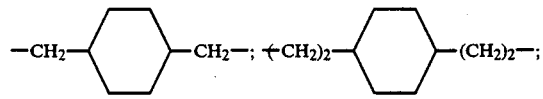

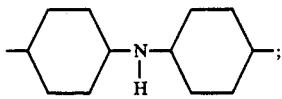

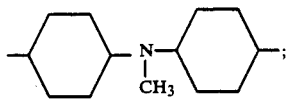

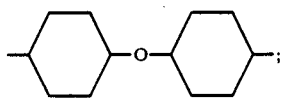

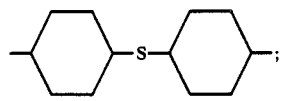

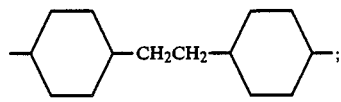

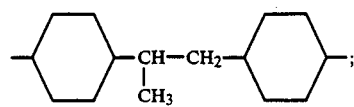

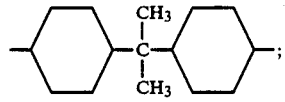

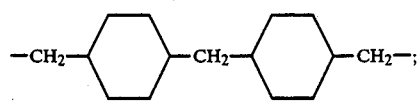

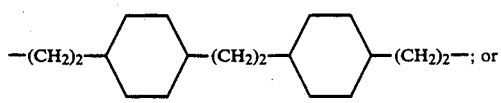

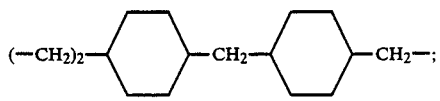

an arylene group of 6–12 group of carbon atoms, or an aralkylene group of 8–14 carbon atoms;

$R^{11}$ is an alkyl group having 1–20 carbon atoms, the group A, or a cycloakylene group of 5–12 carbon atoms;

$R^{12}$ is selected from a lower alkyl or a group —R—Y—H where Y and R are as previously described;

$R^{13}$ is hydrogen; and m is an integer from 1 to 40.

2. A compound of claim 1 wherein $R^1$ is hydrogen and Y is —O—.

3. A compound of claim 2 where B is methylene.

4. A compound of claim 3 wherein m is 1 to 10.

5. A compound of claim 4 wherein B is methylene and $R^2$ is hydrogen.

6. A compound of claim 5 wherein X is the tert-butylamino group, and R is the 2,2-dimethyl-1,3-propylene group.

7. A compound of claim 5 wherein X is the tert-octylamino group, and R is the 2,2-dimethyl-1,3-propylene group.

8. A compound of claim 5 wherein X is the morpholino group, and R is the 2,2-dimethyl-1,3-propylene group.

9. A compound of claim 5 wherein X is the tert-octylamino group, and R is the 1,6-hexylene group.

10. A compound of claim 5 wherein X is morpholino, and R is the 1,6-hexylene group.

* * * * *